United States Patent [19]

Riemenschneider et al.

[11] 3,931,309

[45] Jan. 6, 1976

[54] PROCESS FOR THE PREPARATION OF CARBON TETRACHLORIDE AND PHOSGENE

[75] Inventors: Wilhelm Riemenschneider, Frankfurt am Main; Hans Krekeler, Wiesbaden; Helmut Meidert, Frankfurt am Main, all of Germany

[73] Assignee: Hoechst Aktiengesellschaft, Frankfurt am Main, Germany

[22] Filed: July 6, 1971

[21] Appl. No.: 160,154

[30] Foreign Application Priority Data
July 8, 1970 Germany............................ 2033786
Oct. 5, 1970 Germany............................ 2048841

[52] U.S. Cl............................. 260/544 K; 260/664
[51] Int. Cl.²......................................... C07C 51/58
[58] Field of Search............ 260/664, 544 K, 662 R, 260/658 R, 632

[56] References Cited
UNITED STATES PATENTS
383,992   6/1888   Rumpf................................ 260/664
3,515,752   6/1970   Bauer............................ 260/544 K

*Primary Examiner*—James O. Thomas, Jr.
*Assistant Examiner*—A. Siegel
*Attorney, Agent, or Firm*—Curtis, Morris & Safford

[57] ABSTRACT

A process for the preparation of a mixture of carbon tetrachloride and phosgene in the absence of a catalyst from
a. oxygen-containing carbon-hydrogen compounds or
b. oxygen-containing carbon-hydrogen compounds, carbon monoxide, carbon dioxide, or water, in admixture with aromatic, chlorinated aromatic, chlorinated aliphatic, or chlorinated cyclo-aliphatic hydrocarbons,
with chlorine at an elevated temperature and pressure.

10 Claims, No Drawings

PROCESS FOR THE PREPARATION OF CARBON TETRACHLORIDE AND PHOSGENE

The present invention relates to a process for the preparation of carbon tetrachloride and phosgene.

It has been proposed to prepare carbon tetrachloride by way of pressure chlorolysis of benzene or chlorinated aromatic or chlorinated aliphatic hydrocarbons. If suitable operating conditions are applied, carbon tetrachloride is practically the only product that is formed, while the hexachlorobenzene, which is also formed in a small amount, has to be considered an intermediate product, as it may be recirculated and converted into carbon tetrachloride.

The present invention provides a process for the preparation of a mixture of carbon tetrachloride and phosgene in the absence of catalysts, which comprises reacting a. oxygen-containing carbon-hydrogen compounds or
b. oxygen-containing carbon-hydrogen compounds, carbon monoxide, carbon dioxide, or water, in admixture with aromatic, chlorinated aromatic, chlorinated aliphatic or chlorinated cyclo-aliphatic hydrocarbons, with chlorine at a temperature in the range of from 400° to 800° C and a pressure of between 50 and 800 atmospheres gage.

In the process of the invention it was a surprising fact, which could not have been foreseen, that carbon monixide, carbon dioxide, water or oxygen-containing carbon-hydrogen compounds are converted into phosgene practically quantitatively, in such a way that one oxygen atom corresponds to one molecule of phosgene. The formation of phosgene on the basis of carbon dioxide and/or water, with formation of carbon tetrachloride at the same time, has not been described so far.

The process of the invention has the advantage that phosgene as well as carbon tetrachloride can be produced from such inexpensive components as carbon monoxide, carbon dioxide, mixtures thereof, and, in particular, from water. For example, exhaust gases containing CO and $CO_2$, which may, possibly, also contain water as a result of a process of combustion, may be used in order to produce phosgene in addition to carbon tetrachloride. As the amount of phosgene is directly proportional to the amount of oxygen, it can easily be controlled by adding the desired amounts of carbon monoxide, carbon dioxide or water to the process of chlorination. As a result, the production of carbon tetrachloride can be varied and thus becomes more economical.

The process of the invention also has the advantage that mixtures of oxygen-containing carbon-hydrogen compounds of any origin may be used. Even mixtures containing a great number of compounds practically lead only to the two final products of carbon tetrachloride and phosgene. This is why a complicated separation of the individual components is not necessary. It is a fact of particular significance of the process according to the invention that use may be made of by-products, residues, waste material, rejections and similar material obtained from chemical fabrication processes, as far as they have the required composition. The process of the invention thus ensures a complete utilization of waste material that is mostly causing trouble, while at the same time producing carbon tetrachloride and phosgene which are very important in large-scale industry.

As one molecule of phosgene is formed per atom of oxygen, and carbon tetrachloride is to be obtained at the same time, the oxygen-containing carbon-hydrogen compounds used — if they are used as the only starting material — must have at least one more carbon atom than oxygen atoms in the molecule, i.e. the number of carbon atoms must at least equal the number of oxygen atoms plus one. However, if a mixture of oxygen-containing carbon-hydrogen compounds and aromatic, chlorinated aromatic, chlorinated aliphatic, or chlorinated cyclo-aliphatic hydrocarbons is used, the latter may be considered the starting material for carbon tetrachloride; in this case it is possible to use also those compounds as oxygen-containing carbon-hydrogen compounds that have only one carbon atom per oxygen atom, for example, methanol, ethylene glycol, formaldehyde, formaldehyde polymers and acetic acid.

The oxygen-containing carbon-hydrogen compounds may also be completely or partially substituted by chlorine; there are suitable, for example, alcohols, such as methanol, ethanol or chlorinated ethanols, ethylene glycol, propanol or chlorinated propanols, for example, 1-chlorpropanol-2, butanols or butanol residues obtained, for example, from oxo-syntheses, phenol or phenol-containing substances, quinones, such as anthraquinone, aldehydes, for example, formaldehyde or formaldehyde polymers, acetaldehyde or chloracetaldehyde or condensed acetaldehydes, ketones, such as acetone or chlorine-containing ketones, acids, acid esters, acid anhydrides, ketene and diketene residues, ethers or chlorine-containing ethers, for example, dichlorisopropyl ether or chlorinated diphenyl ethers, epoxides, such as epichlorhydrin residues or ethylene oxide polymers, oxygen-containing heterocycles, such as furane, furane resins, furfural and cumarone resins.

As hydrocarbons there may be used, for example, benzene, toluene, xylene, naphthalene, anthracene, diphenyl, chlorinated aromatic compounds, such as chlorbenzene, dichlorbenzene, polychlorbenzene, mono- and polychlornaphthalene, mono- and polychlordiphenyls, chlorinated aliphatic compounds, such as chloroform, methyl chloride, vinyl chloride, polyvinyl chloride, dichlorethane, hexachlorethane, dichlorpropane, polychlorpropane, completely or partially chlorinated long-chain aliphatic and cyclo-aliphatic hydrocarbons, such as hexachlorcyclohexane or pentachlorcyclopentane.

Both the carbon-hydrogen compounds not containing oxygen and those which contain oxygen may be mixed within their groups, as well as with each other, in any ratio. An admixture of carbon or small amounts of inorganic foreign substances do not adversely affect the reaction process.

The reaction of the carbon and oxygen-containing reactants with chlorine is effected at an elevated temperature and an elevated pressure. The reaction takes place via several steps of chlorination which require different temperatures, so that in most cases there has to be effected a more or less strong initial chlorination in one or several preliminary reaction phases at temperatures in the range of from about 0° to 500° C. Such preliminary reaction phases, which normally take place already at a temperature of less than 250° C, are particularly desirable in the case of slightly or non-chlorinated starting products, since otherwise there can be a coking of the products and thus a choking of the reactor, owing to a chlorine action that is too strong. The actual chlorolytic splitting-up of the C—C bond which leads to the formation of the final products of carbon tetrachloride and phosgene is only brought about at a temperature of more than 400° C with a reaction rate that can be utilized technically. Preference is given to a temperature in the range of from 500° to 700° C. In order to carry out the reaction, a reactor is therefore required which contains, in its inlet section, a preliminary reaction zone having a temperature of up to 400° C, and in its main section a reaction zone having a temperature in the range of from 400° to 800° C. In many cases it is advantageous to keep a liquid sump within the preliminary reaction zone, which sump mainly consists of molten hexachlorbenzene and/or hexachlorethane, into which the reactants are pumped.

The pressure within the reactor is kept between 50 and 800 atmospheres gage, a pressure of between 80 and 300 atmospheres gage being preferred. The pressure in the preliminary reaction phase shall be the same or, optionally, slightly less than the one specified above. The pressure is built up by pumping in the reaction components which are mostly present in the form of liquids. Chlorine, too, is preferably pumped into the reactor in a liquid state. The pressure within the reactor is kept at the desired level by means of a pressure-relieving valve. Within the main reaction zone of the reactor, the reaction components are in supercritical condition, i.e. they are present in the gaseous phase. An exception is presented by hexachlorbenzene, the vapor pressure of which being so small that it may be present in the form of a finely distributed mist in some parts of the reactor.

Chlorine is preferably used in an excess amount. The amount shall be in the range of between 125 and 400 % of the one which is theoretically required for the complete conversion of the hydrocarbons into carbon tetrachloride. Preference is given to an excess of chlorine of between 50 and 100 %, calculated on the theory.

A long reaction tube has proven suitable as a constructional design for the reactor. In its inlet section, following the dosing-in of the reaction components, it is kept at low temperature, serving as preliminary reaction zone, and in its second section it is used as main reaction zone at a temperature of between 400° and 800° C. However, the reactor may also be designed in a different way. Nickel has proven suitable for the lining of the reactor. In this case it is necessary that all reaction components used have only a very low content of sulfur (< 200 ppm).

The chlorination reaction is exothermic. The degree of the nascent heat depends upon the amount of chlorine bound already in the starting material. This is why in most cases an external heating is not necessary after the reaction has started.

The chlorination device may be operated either discontinuously or continuously, the latter being the preferred variant of the process.

The gases leaving the reactor, i.e. excess chlorine, hydrogen chloride, carbon tetrachloride and phosgene, may be separated and purified in known manner, for example, by distillation.

The excess chlorine is advantageously recirculated. The hexachlorbenzene and/or hexachlorethane being formed as byproducts in most cases may also be recirculated and converted completely into carbon tetrachloride. In the case of a continuous operation in a cycle, hexachlorbenzene and/or hexachlorethane may be considered only an intermediate product which does not appear in the final balance.

It becomes evident from the above-mentioned facts that the amount of the phosgene formed in the process depends directly upon the amount of the oxygen-containing carbon-hydrogen compound used. The amount of phosgene can be controlled by the additional pumping-in of oxygen-containing compounds. Thus, if a residue product is used, for example, alcohols, ketones, aldehydes, ethers, acids, or esters may be added in determined doses, if a greater yield of phosgene is to be obtained.

The introduction by doses of carbon monoxide and/or carbon dioxide and/or water into the reactor may be effected either in admixture with the hydrocarbons or in admixture with chlorine. If a separate dosed introduction of the oxygen-containing components into the reactor is chosen, a pumping of the substances in the form of a liquid, close to the inlets of the other components, is preferred. The components may be present in any mixing ratio.

In order to avoid corrosion, it is recommended to heat water by way of a preliminary heater, after it has been brought to the reactor pressure in its liquid form by pumping. The water then enters the reactor in the form of high-pressure steam.

The following Examples serve to illustrate the invention.

EXAMPLE 1

For the reaction there was used a vertical reaction tube made of stainless steel for a nominal pressure of 1.600 atmospheres gage, which had a nickel lining. Its length was 3.300 mm, the outer diameter was 89 mm, and the inner diameter was 40 mm. By way of a different heating, the reaction tube was divided into a preliminary and a main reaction zone. The lower electric jacket heating, which surrounded the reaction tube at a length of 1.100 mm, was heated at a maximum of 250° C. The temperature was measured by means of an inner thermo-electric couple. This section comprising 1.4 liters represented the preliminary reaction zone. The upper electric jacket heating was adjusted in such a way that the inner temperature of the reactor, which was measured by means of a movable thermoelectric couple, was in the range of from 400° to 800°C. This section, which comprised 2.7 liters, represented the main reaction zone. The space-time yield was calculated on this volume. The reaction components of chlorine and the compounds were introduced by pumping, in the form of liquids, at the lower end of the reactor at room temperature by means of a plunger pump. The reaction mixture was drawn off at the top of the reactor and was cooled to about 250° C in a cooler having a nickel lining. At the end of the cooler there was the pressure-relieving valve, by which means the desired pressure was kept inside the reactor. The gases relieved from pressure were at first cooled by way of a pressureless preseparator, which was represented by an empty vessel having a capacity of about 10 liters without any special cooling. In this vessel practically all of the hexachlorbenzene and/or hexachlorethane were separated. The reaction gas was then cooled to about −75° C by means of a coil type refrigerator, in which process carbon tetrachloride and chlorine condensed. The uncondensed hydrogen chloride was measured by means of a gas meter and was analyzed in order to detect any chlorine which had possibly been entrained.
138 g of ethanol and
2.3 kg of chlorine (= 80 % excess)
were introduced per hour by pumping into the apparatus described above at a temperature of 100° C inside the preliminary reaction zone and a temperature of 560° C inside the main reaction zone, and at a pressure of 180 atmospheres gage.

The following reaction products were obtained per hour:

| | |
|---|---|
| 443 g of carbon tetrachloride | (= 96 % of the theory) |
| 290 g of phosgene | (= 98 % of the theory) |
| 25 g of hexachlorethane | (= 3.5 % of the theory) |
| 655 g of hydrogen chloride | (= 100 % of the theory). |

The yield figures in the above and the following Examples were always calculated on the amount of the product that could be figured out theoretically, using the starting material as a reference.

EXAMPLE 2

176 g of acetaldehyde (or an acetaldehyde residue obtained from a distillation process) and
3 kg of chlorine (= 110 % excess)
were pumped per hour into the same apparatus as has been described in Example 1, at a temperature of the preliminary reaction zone of 100° C and a temperature of the main reaction zone of 500° C, and at a pressure of 240 atmospheres gage.

The following reaction products were obtained per hour:

| | |
|---|---|
| 597 g of carbon tetrachloride | (= 97 % of the theory) |
| 390 g of phosgene | (= 98.5 % of the theory) |
| 21 g of hexachlorethane | (= 2.2 % of the theory) |
| 580 g of hydrogen chloride. | |

The hexachlorethane obtained was pumped back into the reactor, in the form of a solution of about 50 % strength in carbon tetrachloride, after the other reaction products had been distilled off. The excess chlorine, which was separated from the other reaction products in an amount of about 1.6 kg per hour, was also pumped back into the reactor.

EXAMPLE 3

203 g of acetone and
3.2 kg of chlorine (= 70 % excess)
were pumped per hour into the same apparatus as has been described in Example 1, at a temperature of the preliminary reaction zone of 150° C and a temperature of the main reaction zone of 660° C, and at a pressure of 80 atmospheres gage.

The following reaction products were obtained per hour:

| | |
|---|---|
| 994 g of carbon tetrachloride | (= 92 % of the theory) |
| 335 g of phosgene | (= 90.5 % of the theory) |
| 51 g of hexachlorethane | (= 6.1 % of the theory) |
| 760 g of hydrogen chloride. | |

EXAMPLE 4

440 g of acetic acid ethyl ester and
5.6 kg of chlorine (= 57 % excess)
were pumped per hour into the same apparatus as has been described in Example 1, at a temperature of the preliminary reaction zone of 100° C and a temperature of the main reaction zone of 550° C, and at a pressure of 400 atmospheres gage.

The reaction was effected in accordance with the equation:

$$CH_3-COO-C_2H_5 + 10\ Cl_2 \rightarrow 2\ CCl_4 + 2\ COCl_2 + 8\ HCl.$$

The following reaction products were obtained per hour:

| | |
|---|---|
| 1495 g of carbon tetrachloride | (= 97 % of the theory) |
| 960 g of phosgene | (= 97 % of the theory) |
| 20 g of hexachlorethane | (= 1.7 % of the theory) |
| 14 g of hexachlorobenzene | (= 1 % of the theory) |
| 1450 g of hydrogen chloride. | |

In the case of continuous operation, the hexachlorethane and hexachlorobenzene, as well as the excess chlorine, were recirculated.

EXAMPLE 5

684 g of β,β'-dichloro-diisopropyl ether and
8.2 kg of chlorine (= 81 % excess)
were pumped per hour into the same apparatus as has been described in Example 1, at a temperature of the preliminary reaction zone of 180° C and a temperature of the main reaction zone of 600° C, and at a pressure of 100 atmospheres gage.

The following reaction products were obtained per hour:

| | |
|---|---|
| 2960 g of carbon tetrachloride | (= 96 % of the theory) |
| 385 g of phosgene | (= 97.5 % of the theory) |
| 28 g of hexachlorethane | (= 3 % of the theory) |
| 1700 g of hydrogen chloride. | |

EXAMPLE 6

A fabrication residue obtained from the preparation of propylene oxide according to the chlorhydrin process, which was composed of:
  1130 g of 1,2-dichloropropane
  252 g of β,β'-dichloro-diisopropyl ether
  76 g of epichlorhydrin
  31 g of 2-methyl-pentene-2-al-1
  25 g of 1,2,3-trichloropropane
  14 g of 1-chloropropanol-2
was pumped per hour, together with 10.5 kg of chlorine (= 67.5 % excess), into the same apparatus as has been described in Example 1, at a temperature of preliminary reaction zone of 200° C and a temperature of the main reaction zone of 600° C, and at a pressure of 80 atmospheres gage.

The following reaction products were obtained per hour:

| | |
|---|---|
| 6260 g of carbon tetrachloride | (= 91.4 % of the theory) |
| 270 g of phosgene | (= 100 % of the theory) |
| 20 g of hexachlorobenzene | (= 0.4 % of the theory) |
| 23 g of hexachlorethane | (= 1.2 % of the theory) |
| 3100 g of hydrogen chloride. | |

After having been separated, the excess chlorine, the hexachlorobenzene and hexachlorethane were pumped back into the reactor and were recirculated.

EXAMPLE 7

A mixture consisting of:
  280 g of phenol
  710 g of monochlorobenzene
  210 g of dichlorobenzene (isomer mixture) and 17.4 kg of chlorine (= 64 % excess)
was pumped per hour into the same apparatus as has been described in Example 1, at a temperature of the preliminary reaction zone of 200° C and a temperature of the main reaction zone of 600° C, and at a pressure of 300 atmospheres gage.

The following reaction products were obtained per hour:

| | |
|---|---|
| 9100 g of carbon tetrachloride | (= 96.5 % of the theory) |
| 290 g of phosgene | (= 99 % of the theory) |
| 60 g of hexachlorobenzene | (= 2 % of the theory) |
| 2000 g of hydrogen chloride. | |

After having been distilled off from carbon tetrachloride, phosgene and hydrogen chloride, the excess chlorine and the hexachlorobenzene formed were recirculated into the reactor.

EXAMPLE 8

A residue mixture obtained from the oxo-synthesis consisting of about 60 % of butanol-2 and 30 % of butanol-1 and approximately 10 % of unknown oxygen-containing compounds, altogether 170 g,
was pumped per hour, together with
390 g of benzene and
13.0 kg of chlorine (= 94 % excess),
into the same apparatus as has been described in Example 1, at a temperature of the preliminary reaction zone of 250° C and a temperature of the main reaction zone of 660° C, and at a pressure of 80 atmospheres gage.

The following reaction products were obtained per hour:

| | |
|---|---|
| 5250 g of carbon tetrachloride | (= 97.8 % of the theory) |
| 160 g of phosgene | (= 100 % of the theory) |
| 22 g of hexachlorobenzene | (= 1.2 % of the theory) |
| 13 g of hexachlorethane | (= 0.9 % of the theory) |
| 1650 g of hydrogen chloride. | |

EXAMPLE 9

A mixture which had been preheated to about 150° C and which consisted of
160 g of cyclohexanol
45 g of cyclohexanone
620 g of hexachloro-cyclohexane (isomer mixture, from which the γ-form had been largely removed) and
7.6 kg of chlorine (= 79 % excess)
was pumped per hour into the same apparatus as has been described in Example 1, without any heating of the preliminary reaction zone, at a temperature of the main reaction zone of 650° C, and at a pressure of 240 atmospheres gage.

The following reaction products were obtained per hour:

| | |
|---|---|
| 3410 g of carbon tetrachloride | (= 95.5 % of the theory) |
| 201 g of phosgene | (= 97.5 % of the theory) |
| 23 g of hexachlorobenzene | (= 1.9 % of the theory) |
| 1200 g of hydrogen chloride. | |

EXAMPLE 10

1000 g of a fabrication residue obtained from the preparation of vinyl chloride being composed of
9.0 % by weight of benzene
2.1 % by weight of chloral
3.5 % by weight of dichloro-dimethylether
29.7 % by weight of dichlorobutene
19.5 % by weight of 1,2-dichlorethane
7.6 % by weight of chlorobenzene
6.9 % by weight of tetrachlorethylene
6.1 % by weight of chloroprene
2.2 % by weight of chloroprene, dimeric
5.8 % by weight od dichloropropene
4.6 % by weight of trichlorethane
3.0 % by weight of chloroxylene and
12.0 kg of chlorine (= 113 % excess)
were pumped per hour into the same apparatus as has been described in Example 1, at a temperature of the preliminary reaction zone of 100° C and a temperature of the main reaction zone of 600° C, and at a pressure of 80 atmospheres gage.

The following reaction products were obtained per hour:

| | |
|---|---|
| 4920 g of carbon tetrachloride | (= 95.12 % of the theory) |
| 40 g of phosgene | (= 90 % of the theory) |
| 31 g of hexachlorobenzene | (= 2.2 % of the theory) |
| 1400 g of hydrogen chloride. | |

EXAMPLE 11

0.88 g of dioxane and 10.0 g of liquid chlorine (= 40 % excess of chlorine) were mixed within a nickel tube that could be tightly closed. The nickel tube had an empty volume of 90 milliliters. It was brought, inside a protecting tube, into an electrical furnace having a temperature of 300° C, was then heated to a temperature of 550° C within 20 minutes and was kept at that temperature for 10 minutes. The tube was then removed from the furnace, was allowed to cool at room temperature and was opened at one end, after the other end had been cooled. In this process mainly hydrogen chloride escaped. The contents of the tube was taken up in pure monochlorobenzene and was analyzed by means of gaschromatography.
2.65 g of carbon tetrachloride and
1.32 g of phosgene were obtained.

If the reaction was carried out according to the reaction equation
$$C_4H_8O_2 + 10\ Cl_2 \rightarrow 2\ CCl_4 + 2\ COCl_2 + 8\ HCl,$$
the yield of carbon tetrachloride was 86 % of the theory and the yield of phosgene was 71 % of the theory. The small yields would have been higher, if part of the products had not been lost by way of entrainment by the evaporated hydrogen chloride. Hexachlorethane or hexachlorobenzene were not found.

EXAMPLE 12

Use was made of the apparatus as has been described in Example 1, however, the upper electric jacket heating was adjusted in such a way that the inner temperature of the reactor was 600° C. In the condensation product, chlorine and hydrogen chloride were determined titrimetrically, while phosgene was determined by gaschromatography.
500 g of benzene having a water content of 0.05 % (that is 0.25 g of $H_2O$) and
11 kg of chlorine having a water content of
32 ppm (that is 0.35 g of $H_2O$)
were pumped per hour into the above-mentioned apparatus at a pressure of 300 atmospheres gage.

The excess of chlorine was 60 % of the theory.

The following reaction products were obtained per hour:

| | |
|---|---|
| 5650 g of carbon tetrachloride | (= 95.3 % of the theory) |
| 3.3 g of phosgene | (= 100 % of the theory) |
| 75 g of hexachlorobenzene | (= 4.1 % of the theory) |
| 1370 g of hydrogen chloride | (= 98 % of the theory) |

The yield figures in the above and the following Examples were always calculated on the amount of the product that could be figured out theoretically, using the starting components of benzene and water as a reference.

The space-time yield was 2090 g of carbon tetrachloride per liter of reaction zone per hour. The hexachlorobenzene was pumped back into the reactor in the form of a solution of about 50 % strength in carbon tetrachloride, after the other reaction products and the excess chlorine had been distilled off. The carbon tetrachloride, phosgene and hydrogen chloride were separated from chlorine by distillation, and the excess chlorine was recirculated into the reactor in an amount of about 4.2 kg per hour.

EXAMPLE 13

500 g of benzene having a water content of 0.05 %
200 g of water which was preheated to 230° C by means of a preheating device after pumping, and which was introduced in doses close to the feed pipe for benzene, and
12 kg of chlorine having a water content of 32 ppm
were pumped per hour into the same apparatus as has been described in Example 1, at a temperature of the preliminary reaction zone of 230°C and a temperature of the main reaction zone of 660° C, and at a pressure of 240 atmospheres gage.

The excess of chlorine was 82 % of the theory.
The following reaction products were obtained per hour:

| | |
|---|---|
| 3980 g of carbon tetrachloride | (= 94.5 % of the theory) |
| 1100 g of phosgene | (= 99.5 % of the theory) |
| 90 g of hexachlorobenzene | (= 4.9 % of the theory) |
| 2200 g of hydrogen chloride | (= 99 % of the theory). |

The calculation of the yield of carbon tetrachloride was based on the fact that a stoichiometrical proportion of the carbon atoms of benzene was used for the formation of phosgene.

The space-time yields were 1475 g/l.h for carbon tetrachloride, and 408 g/l.h for phosgene.

After all the reaction products had been separted, the excess chlorine was pumped back into the reactor.

EXAMPLE 14

800 g of monochlorobenzene
200 g of water and
12.5 kg of chlorine
were pumped per hour into the reactor, under the same conditions as have been specified in Example 13.
The excess of chlorine was 76 % of the theory.
The following reaction products were obtained per hour:

| | |
|---|---|
| 4700 g of carbon tetrachloride | (= 97 % of theory) |
| 1080 g of phosgene | (= 98 % of the theory) |
| 42 g of hexachlorobenzene | (= 2.1 % of the theory) |
| 2000 g of hydrogen chloride | (= 95 % of the theory) |

EXAMPLE 15

2000 g of a mixture consisting of
60 % of hexachlorethane
30 % of trichlorethylene
10 % of tetrachlorethylene,
together with 200 g of water preheated to 230° C and
6 kg of chlorine (= 94 % excess)
were pumped per hour into the reactor, under the same conditions as have been specified in Example 13, however, at a temperature of the main reaction zone of 550° C.

The following reaction products were obtained per hour:

| | |
|---|---|
| 1580 g of carbon tetrachloride | (= 97.5 % of the theory) |
| 1090 g of phosgene | (= 89 % of the theory) |
| 11 g of hexachlorethane | (= 0.9 % of the theory) |
| 10 g of hexachlorobenzene | (= 1.0 % of the theory) |
| 960 g of hydrogen chloride | (= 98.5 % of the theory). |

EXAMPLE 16

500 g of benzene having a water content of 0.05 %
200 g of liquid carbon dioxide from a pressure bottle (the introduction in doses was effected very close to the feed pipe for benzene) and
11 kg of chlorine (water content: 32 ppm)
were pumped per hour into the same apparatus as has been described in Example 1, at a temperature of the preliminary reaction zone of 200° C and a temperature of the main reaction zone of 600° C, and at a pressure of 240 atmospheres gage.

The excess of chlorine was 65 % of the theory.
The following reaction products were obtained per hour:

| | |
|---|---|
| 4850 g of carbon tetrachloride | (= 93.1 % of the theory) |
| 900 g of phosgene | (= 100 % of the theory) |
| 110 g of hexachlorobenzene | (= 6.0 % of the theory) |
| 1350 g of hydrogen chloride | (= 96.5 % of the theory). |

The excess chlorine was recirculated.

EXAMPLE 17

500 g of benzene (water content: 0.05 %)
200 g of carbon monoxide which had been condensed by cooling with liquid air, and which had then been pumped into the reactor in a liquid state by means of a plunger pump, close to the feed pipe for benzene, and
11 kg of chlorine (water content: 32 ppm)
were pumped per hour into the same apparatus as has been described in Example 1, at a temperature of the preliminary reaction zone of 100° C and a temperature of the main reaction zone of 600° C, and at a pressure of 100 atmospheres gage.

The excess of chlorine was 49 %.
The following reaction products were obtained per hour:

| | |
|---|---|
| 5550 g of carbon tetrachloride | (= 93.6 % of the theory) |
| 700 g of phosgene | (= 98.7 % of the theory) |
| 120 g of hexachlorobenzene | (= 6.6 % of the theory) |
| 1360 g of hydrogen chloride | (= 97 % of the theory). |

No carbon monoxide was found in the exhaust gas.
The excess chlorine was recirculated.

The space-time yield was 2060 g of carbon tetrachloride per liter per hour, and 260 g of phosgene per liter per hour.

EXAMPLE 18

A mixture consisting of:
300 g of benzene (water contet: 0.05 %)
200 g of monochlorobenzene
100 g of o-dichlorobenzene and
12 kg of chlorine (water content: 32 ppm)
was pumped per hour into the same apparatus as has been described in Example 1, at a temperature of the preliminary reaction zone of 250° C and a temperature of the main reaction zone of 600° C, and at a pressure of 80 atmospheres gage.

The escess of chlorine was 54 % of the theory.

When after about 3 hours the reactor had reached the thermal balance, a preheated combustion gas which had been compressed to 80 atmospheres gage was additionally introduced in doses at the lower end of the reactor, next to the feed pipe for chlorine, the gas being present in an amount of
250 standard liters per hour comprising
40 % by volume of carbon monoxide
50 % by volume of carbon dioxide and
10 % by volume of water.

The following reaction products were obtained per hour:

|       | 4620 g of carbon tetrachloride | (= 96 % of the theory) |
|-------|--------------------------------|------------------------|
|       | 1610 g of phosgene             | (= 97 % of the theory) |
|       | 56 g of hexachlorobenzene      | (= 2.8 % of the theory) |
| about | 1350 g of hydrogen chloride    | (about 100 % of the theory). |

The excess of chlorine was recirculated, after the reaction products had been separated.

EXAMPLE 19

1000 g of a mixture heated to 160°–170° C, thus melted and composed of:
8 % of water
1 % of benzene
0.4 % of higher chlorinated benzenes
76 % of alpha-hexachloro-cyclohexane
12 % of beta-hexachloro-cyclohexane
1 % of gamma-hexachloro-cyclohexane
0.8 % of delta-hexachloro-cyclohexane
0.8 % of epsilon-hexachloro-cyclohexane and
6.5 kg of chlorine
were pumped per hour into the same apparatus as has been described in Example 1, at a temperature of the preliminary reaction zone of 250° C and a temperature of the main reaction zone of 660° C, and at a pressure of 80 atmospheres gage.

The excess of chlorine was 103 % of the theory.

The following reaction products were obtained per hour:

|       | 2520 g of carbon tetrachloride | (= 95.2 % of the theory) |
|-------|--------------------------------|---------------------------|
|       | 246 g of phosgene              | (= 56 % of the theory)   |
|       | 34 g of hexachlorobenzene      | (= 3.5 % of the theory)  |
| about | 900 g of hydrogen chloride     | (about 100 % of the theory). |

The reduced yield of phosgene was probably to be attributed to the fact that a dehydration to some extent of the product had been taking place, while the hexachloro-cyclohexane-isomer mixture was heated.

What is claimed is:

1. A process for the preparation of a mixture of carbon tetrachloride and phosgene in the absence of catalysts, which comprises reacting
   a. oxygen-containing carbon-hydrogen compounds, in which the number of carbon atoms exceeds the number of oxygen atoms by at least one, or
   b. a compound selected from the group consisting of oxygen-containing carbon-hydrogen compounds, carbon monoxide, carbon dioxide, water, and mixtures thereof, in admixture with a compound selected from the group consisting of benzene, toluene, naphthalene, anthracene, diphenyl, chlorinated compounds thereof, methyl chloride, chloroform, chlorinated alkanes and alkenes of at least two carbon atoms, chlorinated cycloalkanes, and mixtures thereof, with chlorine at a temperature of up to 400°C. in a preliminary reaction zone and continuing the reaction in a main reaction zone at a temperature in the range of from 400° to 800°C. and a pressure of between 50 and 800 atmospheres gage.

2. A process as claimed in claim 1, which comprises using simultaneously carbon monoxide, carbon dioxide and water.

3. A process for the preparation of a mixture of carbon tetrachloride and phosgene in the absence of a catalyst, which comprises reacting an oxygen-containing carbon-hydrogen compound, in which the number of carbon atoms exceeds the number of oxygen atoms by at least one, with chlorine at a temperature of up to 400°C. in a preliminary reaction zone and continuing the reaction in a main reaction zone at a temperature in the range of from 400° to 800°C. and a pressure of between 50 and 800 atmospheres gage.

4. A process as claimed in claim 3, wherein the temperature is in the range of from 500° to 700°C.

5. A process as claimed in claim 3, wherein the pressure is in the range of from 80 to 300 atmospheres gage.

6. A process as claimed in claim 3, which comprises introducing the chlorine into the reactor in a liquid form.

7. A process as claimed in claim 3, which comprises using the chlorine in an excess amount of from 50 to 100 %, calculated on the theory.

8. A process as claimed in claim 7, which comprises recirculating the chlorine.

9. A process as defined in claim 3 in which the oxygen-containing carbon-hydrogen compound is an alcohol, aldehyde, ketone, acid, acid ester, acid anhydride, ether, phenol, quinone, epoxide, oxygen-containing hetero-cycle, or oxygen-containing polymer.

10. A process as defined in claim 3 in which the oxygen-containing carbon-hydrogen compound is ethanol.

* * * * *